(12) United States Patent
Dias et al.

(10) Patent No.: US 7,667,077 B2
(45) Date of Patent: Feb. 23, 2010

(54) POLY-HALOGENATED TRIAZAPENTADIENE COMPOSITIONS

(75) Inventors: H. V. Rasika Dias, Arlington, TX (US); Lorraine G. Van Waasbergen, Arlington, TX (US); Jaime A. Flores, Arlington, TX (US)

(73) Assignee: Board of Regents, The University of Texas, Arlington, TX (US)

( * ) Notice: Subject to any disclaimer, the term of this patent is extended or adjusted under 35 U.S.C. 154(b) by 197 days.

(21) Appl. No.: 11/853,951

(22) Filed: Sep. 12, 2007

(65) Prior Publication Data

US 2009/0069438 A1 Mar. 12, 2009

(51) Int. Cl.
C07C 251/00 (2006.01)
C07C 257/14 (2006.01)
C07C 257/18 (2006.01)
A61K 31/155 (2006.01)
A61K 31/13 (2006.01)

(52) U.S. Cl. .................. 564/243; 564/225; 564/244; 564/248; 564/271; 564/278; 514/631; 514/636; 514/637; 514/638; 514/641

(58) Field of Classification Search ............. None
See application file for complete search history.

(56) References Cited

OTHER PUBLICATIONS

Siedle et al., Oganometallics (2004), 23(10),. p. 2281-2286.*
Database CAPLUS on STN, Acc. No. 1986:553042, Paciorek et al., Journal of Fluorine Chemistry (1985), 30(3), p. 241-250 (abstract).*
Database CAPLUS on STN, Acc. No. 1966:490217, Mazalov et al., Zhurnal Obshchei Khimii (1966), 36(7), p. 1330-1337 (abstract).*
Dias et al., "Antimicrobial Properties of Highly Fluorinated Silver(I) Tris(pyrazolyl)borates," J. Inorganic Biochem. 100 (2006) 158-160.
Dias et al., "Copper(I) Complexes of Fluorinated Triazapentadienyl Ligands: Synthesis and Characterization of [N{$C_3F_7$}C(Dipp)N}$_2$]CuL Where L = $NCCH_3$, $CNBU^t$, CO; Dipp = 2,6-Diisopropylphenyl)," Inorganic Chem. 43 (2004) 5786-5788.
Dias et al., "Monomeric Lithium Triazapentadienyl Complexes," Dalton Trans., 2006 1995-2000.
Dias et al., "Monomeric Thallium(I) Complexes of Fluorinated Triazapentadienyl Ligands," Angew. Chem. Int. Ed., 2005 44, 4907-4910.
Dias et al., "Silver(I) Complexes of a Sterically Demanding Fluorinated Triazapentadienyl Ligand N{$C_3F_7$)C(Dipp)N}$_2$]- Dipp = 2,6-Dissopropylphenyl)," Inorg. Chem. 2004 43, 7396-7402.
Dias et al., "Syntheses of Highly Fluorinated 1,3,5-Triazapentadienyl Ligands and Their Use in the Isolation of Copper(I)-Carbonyl and Copper(I)-Ethylene Complexes," Inorg. Chem. 2006, 45, 8859-8861.
Flores et al., "Gold(I) Ethylene and Copper(I) Ethylene Complexes Supported by a Polyhalogenated Triazapentadienyl Ligand," Inorg. Chem. 2008, 47, 4448-4450.
Siedle et al., "Perfluroalkyl-Substituted Triazapentadienes and Their Metal Complexes," Inorg. Chem. 2003, 42, 932-934.
Siedle et al., "Reactions of the Perfluoroalkyltriazapentadiene $Ph_2N_3C_2(C_3F_7)_2H$ with Acids, Bases, and Water," Inorg. Chem. 2003, 42, 2596-2601.
Siedle et al., "Structure and Dynamics in a Bis(perfluoroalkyl)triazapentadiene Methylmercury Compound," Organometallics, 2004, 23, 2281-2286.

* cited by examiner

*Primary Examiner*—Brian J Davis
(74) *Attorney, Agent, or Firm*—Parks IP Law LLC; La Vonda R. De Witt, Esq.

(57) ABSTRACT

A new class of fluorinated or polyhalogenated triazapentadienes are disclosed. The synthesized triazapentadienes are thermally stable, soluble in typical solvents and have several metal binding sites for complexation with metal ions. The compounds are prepared as colorless crystalline solids. Synthesis takes advantage of a reaction with triethylamine. Synthesized triazapentadienes (with and without complexed metals) inhibit bacterial growth of both Gram positive and Gram-negative bacteria.

24 Claims, 5 Drawing Sheets

POLY-HALOGENATED TRIAZAPENTADIENE COMPOSITIONS

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. CHE 0314666 awarded by the National Science Foundation.

CROSS-REFERENCES TO RELATED APPLICATION

Not applicable.

BACKGROUND OF THE INVENTION

As described, the invention relates generally to the field of chemistry and in particular to the synthesis of a new class of triazapentadiene compounds and compositions formed therefrom.

While triazapentadienes are useful ligands, triazapentadienes with highly fluorinated and other halogenated substituents are rare; perfluorinated compounds have not yet been reported.

SUMMARY OF THE INVENTION

The invention describes a new class of compounds as poly-halogenated triazapentadienes that include fully fluorinated triazapentadienes, chlorinated triazapentadienes and complexed compositions produced therefrom.

The poly-halogenated triazapentadienes disclosed are prepared in high yield, typically as a colorless crystalline solid. The synthesized triazapentadienes are thermally stable and soluble in typical solvents (e.g., toluene, tetrahydrofuran [THF], dichloromethane [$CH_2Cl_2$], diethyl ether [$Et_2O$], hexane, dimethylsulfoxide). The halogen may include fluorine, chlorine, bromine and iodine. The synthesized triazapentadienes and their deprotonated forms (e.g., triazapentadienyl anions) serve as ligands, having, among other things, several metal binding sites for complexation with one or more metal ions. Metal complexed triazapentadienyl fragments may further bind additional molecules, including one or more carbon- or nitrogen-based donor molecules.

In one or more embodiments, described herein are compositions comprising poly-halogenated 1,3,5 triazapentadiene, wherein the composition is thermally stable, electron-poor and accommodates sterically demanding substituents on both 2- and 6-positions of N-aryl groups. Such composition may further coordinate with one or more metal ions. In one form, compositions are metal triazapentadienyl ligands and binds a carbon- or nitrogen-based donor molecule. The compositions may be a ligand for metal coordination chemistry. The compositions are typically weak donors. The compositions inhibit growth of Gram positive and Gram negative bacteria.

In additional embodiments are provided one or more compositions comprising a poly-halogenated 1,3,5 triazapentadiene with electron deficient primary amines, wherein the composition is prepared by a reaction with a tertiary amine as a base. Such compositions may be from a reaction that includes $C_6F_5NH_2$, $C_3F_7$—CF=N—$C_4F_9$ and triethylamine in a molar ratio at or about 2:1:3 or $C_6F_5NH_2$, $CF_3$—CF=N—$C_2F_5$ and triethylamine in a molar ratio at or about 2:1:3. Such compositions include [N{($C_3F_7$)C($C_6F_5$)N}$_2$]H, [N{($CF_3$)C($C_6F_5$)N}$_2$]H, [N{($C_3F_7$)C(2-F,6-($CF_3$)$C_6H_3$)N}$_2$]H and [N{($C_3F_7$)C(2,6-$Cl_2C_6H_3$)N}$_2$]H. The compositions may complex with a metal to form a metal triazapentadienyl. Examples of these include [N{($C_3F_7$)C($C_6F_5$)N}$_2$]Cu(CO) (NCCH$_3$), [N{($C_3F_7$)C(2-F,6-($CF_3$)$C_6H_3$)N}$_2$]CuCO, [N{($C_3F_7$)C($C_6F_5$)N}$_2$]CuNCCH$_3$, [N{($C_3F_7$)C($C_6F_5$)N}$_2$]Cu($C_2H_4$), [N{($C_3F_7$)C(2-F,6-($CF_3$)$C_6H_3$)N}$_2$]Cu(CO) (NCCH$_3$), [N{($C_3F_7$)C(2-F,6-($CF_3$)$C_6H_3$)N}$_2$]CuNCCH$_3$, {[N{($C_3F_7$)C($C_6F_5$)N}$_2$]Ag}$_n$, [N{($C_3F_7$)C($C_6F_5$)N}$_2$]Ag, [N{($C_3F_7$)C(2-F,6-$CF_3C_6H_3$)N}$_2$]Ag, and [N{($C_3F_7$)C(2,6-$Cl_2C_6H_3$)N}$_2$]Ag. Such compositions may be a metal triazapentadienyl adduct that binds a carbon- or nitrogen-containing donor.

Generally, compositions herein include a compounds as described below.

in which $R^1$ may be an alkyl or aryl groups and $R^2$ may be a fluoro alkyl group. Such compositions are effective as antibacterial agents.

In further embodiments are provided a ligand for metal coordination chemistry comprising:

wherein $R^1$ is an alkyl or aryl group and $R^2$ is a fluoro alkyl group and wherein the composition has coordination centers for complexation with a metal ion. The metal ion is introduced in a solvent. Such solvents may include acetonitrile or tetrahydrofuran. The ligands when complexed are capable of further complexation with a second molecule having one or more donors. Examples include but are not limited to carbon monoxide, ethylene, acetonitrile, and phosphine.

A synthetic pathway for a new class of poly-halogenated triazapentadienes is disclosed herein. Synthesis takes advantage of a reaction with triethylamine as compared with previous unsuccessful and/or highly inefficient (very low yield) synthetic routes that have relied on a reaction with excess primary amines.

Compositions herein are typically obtained by a reaction comprising:

wherein $R^1$ is an alkyl or aryl group and $R^2$ is a fluoro alkyl group. $R^1$ is typically selected from the group consisting of $C_6F_5$, 2-F,6-$(CF_3)C_6H_3$; 3,5-$(CF_3)_2C_6H_3$; 2,6-$Cl_2C_6H_3$; CH(Me)Ph; 2,6-(i-Pr)$_2C_6H_3$ and 2,4,6-$(Me)_3C_6H_2$, wherein Me is methyl, Ph is phenyl. $R^2$ is typically $CF_3$ and $C_3F_7$. Products of such a reaction typically produce compositions as described herein in high yield as a colorless crystalline solid. When $R^2$ is $C_3F_7$, the reaction includes $C_6F_5NH_2$, $C_3F_7$—CF=N—$C_4F_9$ (obtained from tri(perfluorobutyl)amine, $(C_4F_9)_3N$, precursor) and triethylamine in a molar ratio at or about 2:1:3. When $R^2$ is $CF_3$, the reaction includes $C_6F_5NH_2$, $CF_3$—CF=N—$C_2F_5$ (obtained from tri(perfluoroethyl) amine, $(C_2F_5)_3N$, precursor) and triethylamine in a molar ratio at or about 2:1:3.

Methods described herein produce compounds that inhibit growth of Gram-positive and Gram-negative bacteria. A suitable method includes providing a composition comprising as an antibacterial agent. Examples of Gram positive bacteria that are inhibited are *Staphylococcus aureus* and *Pseudomonas aeruginosa*. Gram positive bacteria that are inhibited by compounds described herein include *Bacillus subtilis* and *Escherichia coli*.

The synthesized triazapentadienes (with and without complexed metals) as described herein inhibit bacterial growth of both Gram positive and Gram-negative bacteria.

Those skilled in the art will further appreciate the above-noted features and advantages of the invention together with other important aspects thereof upon reading the detailed description that follows in conjunction with the drawings.

BRIEF DESCRIPTION OF THE FIGURES

For more complete understanding of the features and advantages of the present invention, reference is now made to the detailed description of the invention along with the accompanying figures, wherein.

DETAILED DESCRIPTION OF THE INVENTION

The invention, as defined by the claims, may be better understood by reference to the following detailed description. The description is meant to be read with reference to the figures contained herein. This detailed description relates to examples of the claimed subject matter for illustrative purposes, and is in no way meant to limit the scope of the invention. The specific aspects and embodiments discussed herein are merely illustrative of ways to make and use the invention, and do not limit the scope of the invention.

Figure 1A:
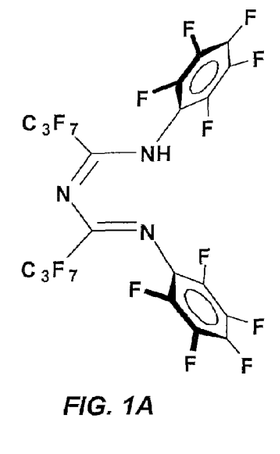
FIGS. 1A-1B depict representative structures for 1,3,5-triazapentadiene molecules described herein.
Figure 1B:
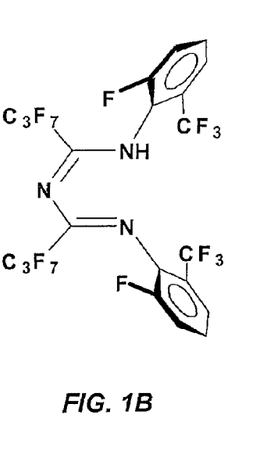
Figure 1C:
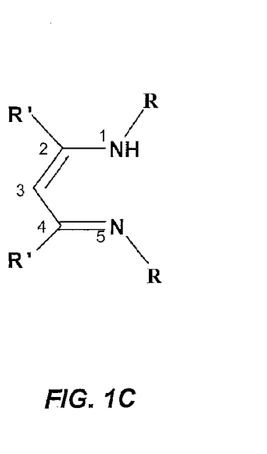
FIG. 1C depicts a structure from another class of compounds known as 1,5-diazapentadiene.
Figure 2:
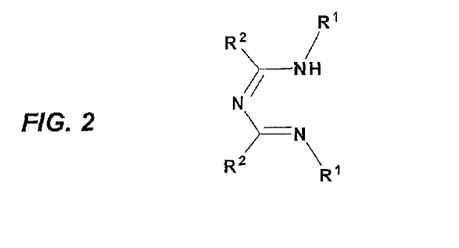
FIG. 2 depicts a representative triazapentadiene composition as described herein.

Described herein poly-halogenated triazapentadienes, including a fully fluorinated triazapentadiene and a highly fluorinated triazapentadiene as depicted in FIGS. 1A and 1B. The new class of compounds described herein are related to a popular class of compounds known as diazapentadienes that may also be fluorinated (FIG. 1C). Accordingly, compounds disclosed herein are referred generally as 1,3,5-triazapentadienes as shown in FIG. 2 in which $R^1$ may be a alkyl or aryl group and $R^2$ may be a fluoro alkyl group. Examples of $R^1$ include $C_6F_5$, 2-F,6-$(CF_3)C_6H_3$; 3,5-$(CF_3)_2C_6H_3$; 2,6-$Cl_2C_6H_3$; CH(Me)Ph; 2,6-(i-Pr)$_2C_6H_3$ and 2,4,6-$(Me)_3C_6H_2$, wherein Me is methyl, Ph is phenyl. Examples of $R^2$ include $CF_3$ and $C_3F_7$. Such compounds may be halogenated with one or more halogen groups that include fluorine, chlorine, bromine and or iodine.

As a new class of compounds, the poly-fluorinated triazapentadienes, fully fluorinated triazapentadienes and other poly-halogenated triazapentadienes compositions described herein are different from previously disclosed but related compositions, such as 1,5-diazapentadiene.

Figure 3:
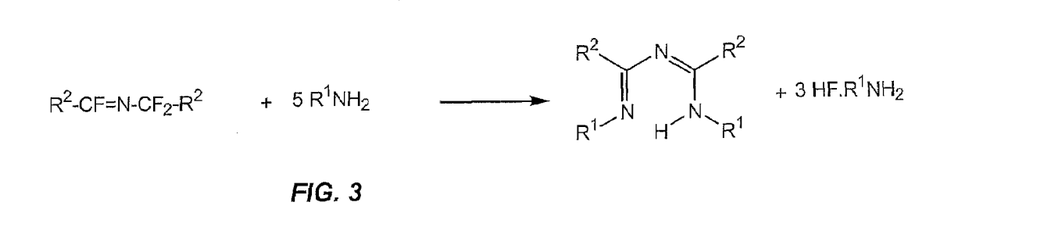
FIG. 3 depicts a prior typical synthetic route to form another related class of compounds.

While a previous synthetic route had been used to form some of the related compounds—a reaction which relied on excess primary amines (FIG. 3)—such a reaction was unsuited for forming the new class of compounds disclosed herein, which includes triazapentadienes with electron deficient primary amines, and also produced compounds of very low yield.

Figure 4:
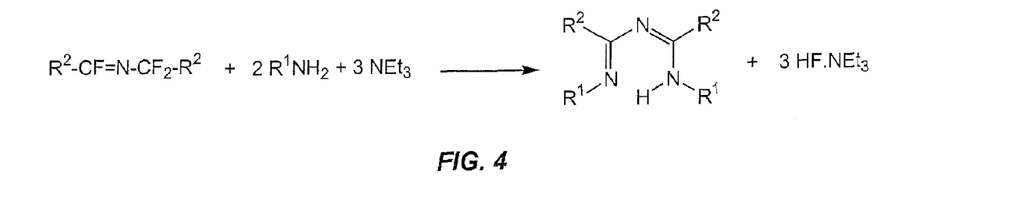
FIG. 4 depicts a synthetic route for forming a triazapentadiene as described herein.

Triazapentadienes with electron deficient primary amines are prepared herein by a suitable reaction that includes a tertiary amine as the base. A preferred synthetic route is depicted in FIG. 4, wherein $R^1$ and $R^2$ are as described above. In one example, $C_6F_5NH_2$ with $C_3F_7$—CF=N—$C_4F_9$ and triethylamine are combined in a molar ratio at or about 2:1:3. In another example, $C_6F_5NH_2$, $CF_3$—CF=N—$C_2F_5$ (obtained from tri(perfluoroethyl)amine, $(C_2F_5)_3N$, precursor) and triethylamine are combined in a molar ratio at or about 2:1:3. Formed compounds include, but are not limited to, $[N\{(C_3F_7)C(C_6F_5)N\}_2]H$ and $[N\{(C_3F_7)C(2-F,6-(CF_3)C_6H_3)N\}_2]H$.

Formed triazapentadienyl compositions described herein are thermally stable, usually electron-poor and may have sterically demanding substituents on both 2- and 6-positions of N-aryl groups. Examples of representative formed compounds are shown FIGS. 4-11.

Figure 5:
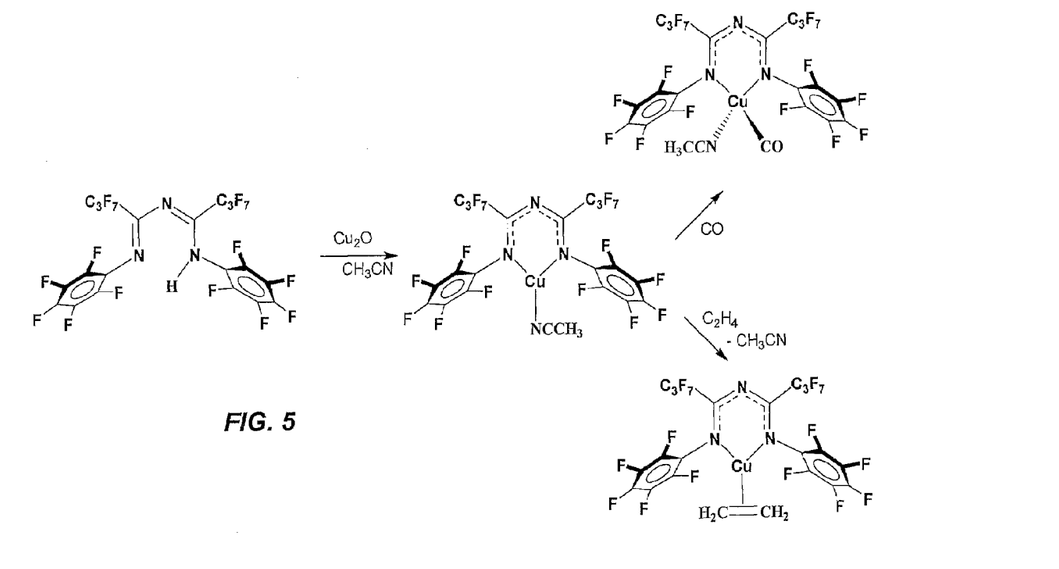
FIG. 5 depicts a metal complexation reaction for triazapentadienes as described herein.
Figure 6:
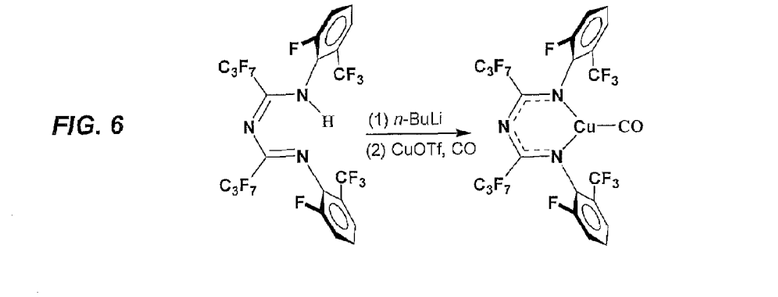
FIG. 6 depicts another metal complexation reaction of a polyhalogenated triazapentadienyl ligand as described herein.

The synthesized triazapentadienes described herein serve as ligands and form metal complexes with specific coordinated centers. For example, a metal ion, such as copper or silver is introduced in acetonitrile or in tetrahydrofuran (THF). After metal complexation, a metal-complexed triazapentadienyl composition is capable of further complexation with other molecules having one or more donors (e.g., C-, N-, P-based molecules, such as CO, ethylene, acetonitrile, phosphine). A first example of a metal complexation reactions are shown in FIG. 5. Another example of a metal complexation reaction is shown in FIG. 6.

Figure 7:
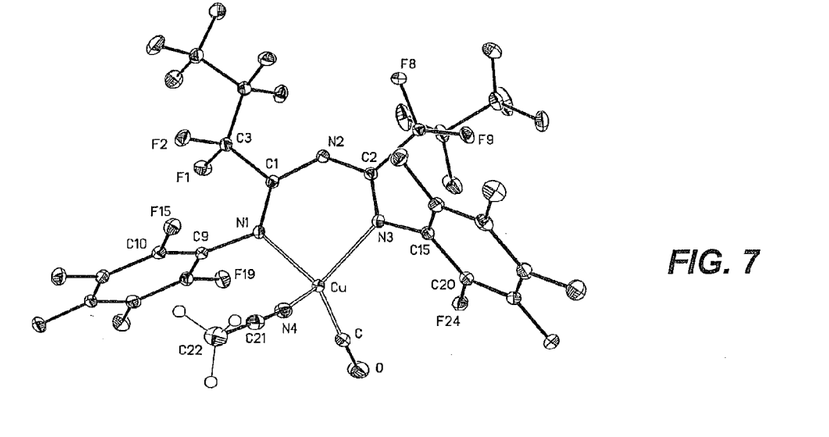
FIG. 7 depicts an X-ray structure of a metal complexed triazapentadiene composition described herein.

In FIG. 5, the initial triazapentadiene composition, [N{($C_3F_7$)C($C_6F_5$)N}$_2$]H, was first complexed with $Cu_2O$ as a source for the copper (Cu) ion to form [N{($C_3F_7$)C($C_6F_5$)N}$_2$]CuNCCH$_3$. The metal complex [N{($C_3F_7$)C($C_6F_5$)N}$_2$]CuNCCH$_3$ was further reacted with carbon monoxide (CO, at 1 atm) in $CH_2Cl_2$ leading to [N{($C_3F_7$)C($C_6F_5$)N}$_2$]Cu(CO)(NCCH$_3$) as depicted in FIG. 7 or reacted with ethylene (at 1 atm) in dichloromethane leading to [N{($C_3F_7$)C($C_6F_5$)N}$_2$]Cu($C_2H_4$) as depicted in FIG. 8. Selected bond lengths of the structure of FIG. 7 (in Angstroms [Å]) and angles (degrees, in parenthesis) include: Cu—C 1.8333(17); Cu—N(4) 2.0183 (14); Cu—N(1) 2.0232 (12); Cu—N(3) 2.0499(12); O—C 1.124(2), N(1)-Cu—N(3) 91.04 (5); and O—C—Cu 176.68 (16). Selected bond lengths of the structure of FIG. 8 in Å and angles (degrees, in parenthesis) include: Cu—N(3) 1.946(2); Cu—N(1) 1.955 (2); Cu—C(21) 2.010(3); Cu—C(22) 2.018 (3); C(21)-C(22) 1.364 (4); N(3)-Cu—N(1) 96.66 (9).

Figure 9:
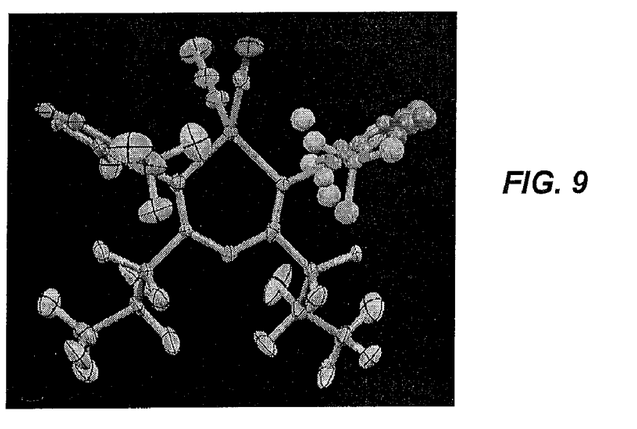
FIG. 9 depicts an X-ray structure of still another metal-complexed triazapentadiene composition described herein.

Interestingly, with the composition of FIG. 7, the acetonitrile remained bonded to the copper(I) in the carbonyl adduct as evident from the spectroscopic and X-ray crystallographic data (vide infra). [N{($C_3F_7$)C(2-F,6-($CF_3$)$C_6H_3$)N}$_2$]Cu(CO)(NCCH$_3$) was also prepared using a similar route and the complexed composition also retained acetonitrile (see FIG. 9).

Referring to FIG. 7, the copper center is four-coordinate and adopts a pseudo tetrahedral geometry. The triazapentadienyl ligand binds to the metal center in a $\kappa^2$-fashion. Similarly, [N{($C_3F_7$)C(2-F,6-($CF_3$)$C_6H_3$)N}$_2$]Cu(CO)(NCCH$_3$) also features a four-coordinate copper center (see FIG. 9). For [N{($C_3F_7$)C(2-F,6-($CF_3$)$C_6H_3$)N}$_2$]Cu(CO)(NCCH$_3$), the Cu—C distance and Cu—C—O angle are 1.846(3) Å and 177.0(4)°, respectively.

Figure 8A:
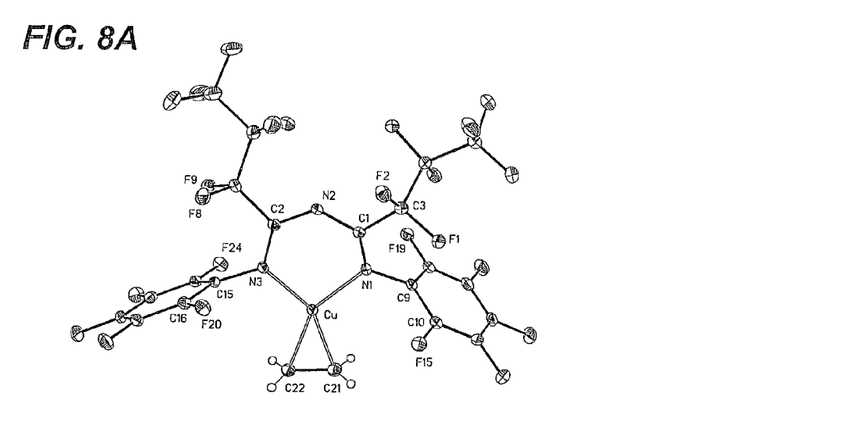
FIGS. 8A and 8B depict (A) X-ray structure and (B) ball and stick molecular structure of another metal complexed triazapentadiene composition described herein.
Figure 8B:
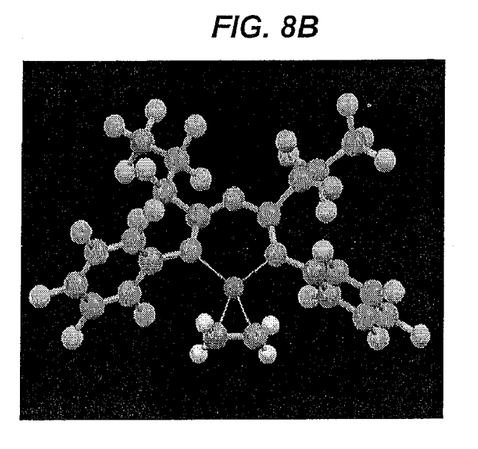

Referring to FIG. 8, the copper center is three-coordinate and the X-ray structure of [N{($C_3F_7$)C($C_6F_5$)N}$_2$]Cu($C_2H_4$) (FIG. 8A) shows the ethylene molecule coordinates to copper (I) in an $\eta^2$-fashion. The $^1$H NMR spectrum of [N{($C_3F_7$)C($C_6F_5$)N}$_2$]Cu($C_2H_4$) in $C_6D_6$ showed the ethylene signal at δ 3.27, which is a significant upfield shift relative to a corresponding peak of free ethylene (δ 5.24). With this composition, treatment with excess ethylene led to a disappearance of the bound ethylene signal, indicating fast exchange with free ethylene on the NMR timescale. The ethylene carbon signal of [N{($C_3F_7$)C($C_6F_5$)N}$_2$]Cu($C_2H_4$) in $^{13}$C{$_1$H} NMR spectrum is observed at δ 86.1. A corresponding peak in free ethylene appears at a much higher frequency (δ 123.5). The C=C bond distance of the coordinated ethylene (1.364(4) Å) of FIG. 8 is identical to that found in [HC{($CH_3$)C(2,6-Me$_2C_6H_3$)N}$_2$]Cu($C_2H_4$) (1.365(3) Å)—a related diazapentadienyl system—and marginally longer as compared to that of free ethylene. The nitrogen to copper distances of [N{($C_3F_7$)C($C_6F_5$)N}$_2$]Cu($C_2H_4$) (1.946(2), 1.955 (2) Å) were much shorter compared to those observed for the [N{($C_3F_7$)C($C_6F_5$)N}$_2$]Cu(CO)(CH$_3$CN). This may be primarily a steric effect because the former has a 3-coordinate metal site (vs. 4-coordinate in the latter). The Cu—N distances of [N{($C_3F_7$)C($C_6F_5$)N}$_2$]Cu($C_2H_4$) are similar to those seen with 3-coordinate [N{($C_3F_7$)C(2-F,6-($CF_3$)$C_6H_3$)N}$_2$]CuCO.

Figure 10A:
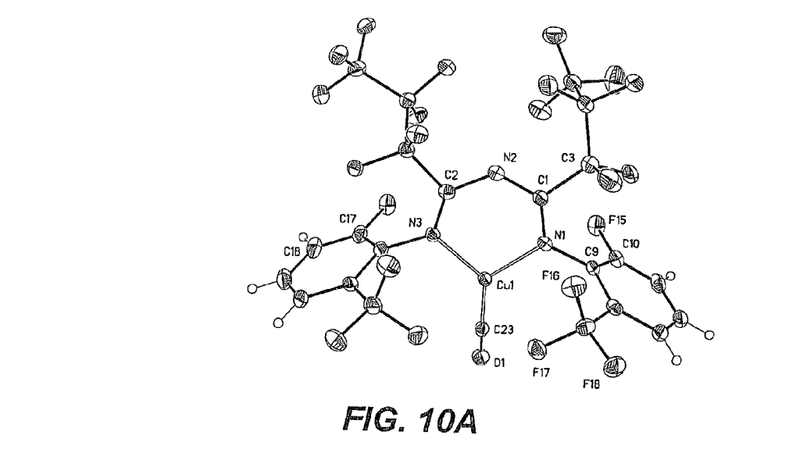
FIG. 10A depicts an X-ray structure of still another metal complexed triazapentadienes composition described herein.
Figure 10B:
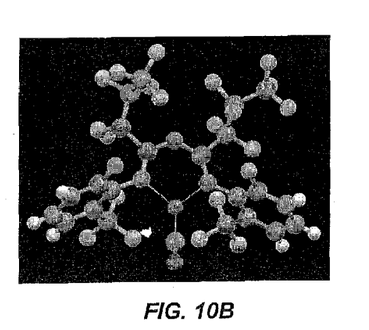
FIGS. 10B and 10C depict ball and stick molecular structures of complexed triazapentadiene compositions described in FIG. 10A.
Figure 10C:
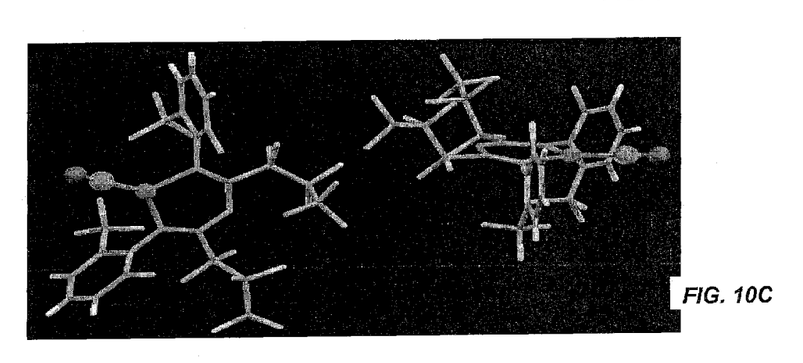

In another metal complexation example depicted in FIG. 6, an initial triazapentadiene composition is [N{($C_3F_7$)C(2-F,6-($CF_3$)$C_6H_3$)N}$_2$]H and reacted as a lithium salt, [N{($C_3F_7$)C(2-F,6-($CF_3$)$C_6H_3$)N}$_2$]Li, with CuOTf and CO (at 1 atm) in THF. The x-ray structure formed by the reaction of FIG. 10 is a three coordinate metal complex, [N{($C_3F_7$)C(2-F,6-($CF_3$)$C_6H_3$)N}$_2$]CuCO, that crystallized in the P2$_1$/n space group with two chemically similar molecules in an asymmetric unit (the relative orientation of the $C_3F_7$ groups is the only key difference between the two, as depicted in FIG. 10C) and included a trigonal planar copper site.

IR spectra of [N{($C_3F_7$)C($C_6F_5$)N}$_2$]Cu(CO)(NCCH$_3$) and [N{($C_3F_7$)C(2-F,6-($CF_3$)$C_6H_3$)N}$_2$]Cu(CO)(NCCH$_3$) show that $v_{co}$ bands of the exemplified compositions appear at 2108 and 2119 cm$^{-1}$, respectively. A three coordinate [N{($C_3F_7$)C(2-F,6-($CF_3$)$C_6H_3$)N}$_2$]CuCO had a much higher $v_{co}$ at 2128 cm$^{-1}$. The acetonitrile ligand appears to reduce acidity at the copper site. Yet, $v_{co}$ values of all complexed compositions were high and closer to that of free CO, which is 2143 cm$^{-1}$, indicating a presence of acidic copper sites with poor Cu→CO π-backbonding and a weak donating nature of the formed polyfluorinated triazapentadienyl ligands described (see TABLE 1). TABLE 1 illustrates representative structural and spectroscopic parameters for copper-carbonyl compounds described herein. Bond distance data is given for representative compounds based on structural characterization.

TABLE 1

| Compound | $v_{CO}$ in cm$^{-1}$ KBr | $v_{CO}$ in cm$^{-1}$ Nujol | Cu—C (Å) |
|---|---|---|---|
| [N{($C_3F_7$)C($C_6F_5$)N}$_2$]Cu(CO)(NCCH$_3$) | 2108 | 2107 | 1.8333 |
| [N{($C_3F_7$)C(2-F,6-($CF_3$)$C_6H_3$)N}$_2$]Cu(CO)(NCCH$_3$) | 2119 | 2118 | 1.846 |
| [N{($C_3F_7$)C(2-F,6-($CF_3$)$C_6H_3$)N}$_2$]CuCO | 2128 | 2120 | 1.815 |

Complexed compositions described herein, such as [N{($C_3F_7$)C($C_6F_5$)N}$_2$]Cu(CO)(NCCH$_3$), [N{($C_3F_7$)C(2-F,6-($CF_3$)$C_6H_3$)N}$_2$]CuCO, and [N{($C_3F_7$)C($C_6F_5$)N}$_2$]Cu($C_2H_4$), may be dried under reduced pressure without losing CO or ethylene; [N{($C_3F_7$)C(2-F,6-($CF_3$)$C_6H_3$)N}$_2$]Cu(CO)(NCCH$_3$) may lose CO under similar conditions to give [N{($C_3F_7$)C(2-F,6-($CF_3$)$C_6H_3$)N}$_2$]CuNCCH$_3$. The loss of a ligand (e.g., CO) in the latter compound may be a steric effect of such a bulkier triazapentadienyl composition. $CH_2Cl_2$ solutions comprising a complexed composition (e.g., Cu—CO complexed compositions or ethylene complexed compositions) turned green with time when exposed to air. Solid samples of such compositions (e.g., Cu—CO and Cu—$C_2H_4$ complexes) may be handled in air for short periods without any apparent decomposition.

Unless otherwise noted, all synthetic manipulations were carried out under an atmosphere of purified nitrogen using standard Schlenk techniques. Solvents were purchased from commercial sources, distilled from conventional drying agents, and were degassed by a freeze-pump-thaw method known to one of ordinary skill in the art. Glassware was oven-dried at 150° C. overnight. NMR spectra were recorded at 25° C. on a 500 and 300 MHz spectrometer ($^1$H, 500.16 MHz or 300.53 MHz; and $^{19}$F: 470.62 MHz or 282.78 MHz). Proton chemical shifts were reported in ppm versus Me$_4$Si. $^{19}$F NMR chemical shifts were referenced relative to external CFCl$_3$. Melting points were obtained on a suitable melting apparatus and readings were not corrected. Elemental analyses of CHN were performed a suitable analyzer. Pentafluoroaniline, 2-fluoro,6-trifluoromethylaniline, triethylamine, $Cu_2O$, $(CuOTf)_2$.benzene, carbon monoxide, and ethylene were purchased from commercial sources. Perfluoro-5-aza-4-nonene was synthesized using a published procedure (e.g., Siedle, et al. Inorg. Chem. 2003; 42:932).

For synthesis of $[N\{(C_3F_7)C(C_6F_5)N\}_2]H$, perfluoro-5-aza-4-nonene (1.00 g, 2.30 mmol) was added dropwise to a mixture of triethylamine (0.69 mL, 6.90 mmol) and pentafluoroaniline (0.84 g, 4.6 mmol) in ether at 0° C. After addition, the solution was stirred overnight at room temperature. Nitrogen atmosphere was not necessary after this point. The mixture was then filtered; filtrate was collected and washed with 10% HCl and then twice with deionized water. The ether layer was separated and dried over $CaCl_2$. The solvent was removed under reduced pressure to obtain a white powder which was recrystallized from $CH_2Cl_2$ at −25° C. to obtain colorless crystals of $[N\{(C_3F_7)C(C_6F_5)N\}_2]H$ in 85% yield. Melting point (Mp) was 104-105° C. $^{19}F$ NMR ($CDCl_3$): δ 80.00 (apparent triplet, J=8.4 Hz, 9.8 Hz, $CF_3$), −80.37 (apparent triplet, J=8.4 Hz, 9.8 Hz, $CF_3$), −115.08 (br, α-$CF_2$), −116.72 (s, α-$CF_2$), −124.85 (br, β-$CF_2$), −126.44 (s, β-$CF_2$), −144.82 (d, J=17.2 Hz, o-F), −148.0 (d, J=19.5 Hz, o-F), −149.54 (t, J=20.9 Hz, p-F), −159.44 (t, J=21.8 Hz, p-F), −159.80 (t, J=18.3 Hz, m-F), −162.90 (td, J=21.2 Hz, 6.6 Hz, m-F). $^1H$ NMR ($CDCl_3$): δ 6.91 (s, 1H, NH). Elemental analysis for $C_{20}HF_{24}N_3$: (a) Calculated: C, 32.50; H, 0.14; N, 5.68; (b) Found: C, 31.98; H, 0.41; N, 5.72.

For synthesis of $[N\{(C_3F_7)C(C_6F_5)N\}_2]Cu(CO)(CH_3CN)$, $[N\{(C_3F_7)C(C_6F_5)N\}_2]H$ (0.50 g, 0.67 mmol) and $Cu_2O$ (0.05 g, 0.34 mmol) were mixed in acetonitrile and refluxed overnight. The resulting solution was filtered through a bed of a filter agent (e.g., standard supercell); filtrate was collected and solvent removed under reduced pressure to obtain crude $[N\{(C_3F_7)C(C_6F_5)N\}_2]CuNCCH_3$ as an oil, which was crystallized from hexane-$Et_2O$ mixture and used directly in the next step. $[N\{(C_3F_7)C(C_6F_5)N\}_2]CuNCCH_3$ was dissolved in $CH_2Cl_2$ and CO was bubbled through the solution followed by stirring for 30 minutes. When solvent was removed under reduced pressure crude $[N\{(C_3F_7)C(C_6F_5)N\}_2]Cu(CO)(CH_3CN)$ was obtained which was dissolved in ether and cooled to −25° C. to obtain pale yellow crystals. Yield was 77%. Mp.: 92-94° C. $^{19}F$ NMR ($CDCl_3$): δ −162.94 (td, J=24.0 Hz, 6.6 Hz, m-F), −160.00 (t, J=19.5 Hz, m-F), −159.52 (t, J=22.8 Hz, p-F), −149.74 (t, J=20.4 Hz, p-F), −147.99 (d, J=19.5 Hz, o-F), −144.80 (d, J=17.2 Hz, o-F), −126.49 (s, β-$CF_2$), −124.83 (br, β-$CF_2$), −116.77 (s, α-$CF_2$), −115.12 (br, α-$CF_2$), −80.38 (apparent triplet, J=7.6 Hz, 10.8 Hz, $CF_3$), −80.01 (apparent triplet, J=7.6 Hz, 10.8 Hz, $CF_3$). $^1H$ NMR ($CDCl_3$): δ 1.87 (s, 3H, $CH_3CN$). Elemental analysis for $C_{23}H_3CuF_{24}N_4O$: (a) Calculated: C, 31.72; H, 0.35; N, 6.43; (b) Found: C, 29.80; H, 0.80; N, 5.19. IR (KBr, $cm^{-1}$): 2108 (CO).

For synthesis of $[N\{(C_3F_7)C(C_6F_5)N\}_2]Cu(C_2H_4)$, $[N\{(C_3F_7)C(C_6F_5)N\}_2]CuNCCH_3$ was prepared as described above, dissolved in $CH_2Cl_2$ and ethylene was bubbled into the solution for about 3 minutes. After stirring for 30 minutes, the solvent was removed under vacuum. The resulting residue was dissolved in hexane and cooled to −25° C. to obtain needle shaped crystals. Yield: 92%. Mp: 120-122° C. $^{19}F$ NMR ($CDCl_3$): δ −80.23 (t, J=9.8 Hz, $CF_3$), −109.02 (d, J=8.5 Hz, α-$CF_2$), −124.24 (s, β-$CF_2$), −148.32 (d, J=20.7 Hz, o-F), −157.98 (t, J=21.6 Hz, p-F), −161.57 (td, J=21.8 Hz, 5.3 Hz, m-F), $^1H$ NMR ($CDCl_3$): δ 3.86 (s, 4H, $C_2H_4$). $^1H$ NMR ($C_6D_6$): δ 3.07 (s, 4H, $C_2H_4$). $^{13}C\{^1H\}$ NMR ($CDCl_3$), selected: δ 86.1 (s, $C_2H_4$). Elemental analysis for $C_{22}H_4F_{24}N_3Cu$: (a) Calculated: C, 31.84; H, 0.49; N, 5.06.; (b) Found: C, 32.27; H, 0.57; N, 5.26.

For synthesis of $[N\{(C_3F_7)C(2-F,6-(CF_3)C_6H_3)N\}_2]H$, perfluoro-5-aza-4-nonene (1.00 g, 2.31 mmol) was added dropwise to a solution of 2-fluoro,6-trifluoromethylaniline (0.827 g, 4.62 mmol) and triethylamine (1.0 mL, 7.18 mmol) in ether (15 mL) at −5° C. This solution was allowed to warm to room temperature and stirred for 3 days (a precipitate and formation of two phases were observed after 12 hours). Inert atmosphere was not required. The resulting mixture was washed once with 10% HCl and twice with deionized water. The organic layer was separated and dried over $CaCl_2$. The solvent was removed under reduced pressure to obtain a yellow oily composition. Pentane was added and cooled to −15° C. to obtain $[N\{(C_3F_7)C(2-F,6-(CF_3)C_6H_3)N\}_2]H$ as a white precipitate. It could be recrystallized from $CH_2Cl_2$ at −15° C. Yield: 52%. Mp: 77-83° C. $^{19}F$ NMR ($CDCl_3$): δ −61.66 and −61.70 (s, 6F, o-$CF_3$), −79.98 (t, J=9.8 Hz, 3F, $CF_3$), −80.43 (t, J=8.7 Hz, 3F, $CF_3$), −115.37 (s, 2F, α-$CF_2$), −119.54 (s, 2F, α-$CF_2$), −124.60 (br, 2F, o-F), −126.34 (s, 4F, β-$CF_2$). $^1H$ NMR ($CDCl_3$): δ 7.51 (apparent doublet, J=2.75 Hz, 2H), 7.36 (m, 2H), 7.13 (m, 2H), 6.55 (s, 1H, NH). Elemental analysis for $C_{22}H_7F_{22}N_3$: (a) Calculated: C, 36.13; H, 0.96; N, 5.75; (b) Found: C, 35.74; H, 1.00; N, 5.86.

For synthesis of $[N\{(C_3F_7)C(2-F,6-(CF_3)C_6H_3)N\}_2]Cu(CO)(NCCH_3)$, $[N\{(C_3F_7)C(2-F,6-(CF_3)C_6H_3)N\}_2]H$ (0.500 g, 0.684 mmol) and $Cu_2O$ (0.059 g, 0.410 mmol) were mixed in acetonitrile (15 mL) and heated overnight at 90° C. The reaction mixture was filtered, and solvent was removed from the filtrate under reduced pressure. A resulting oily product ($[N\{(C_3F_7)C(2-F,6-(CF_3)C_6H_3)N\}_2]CuNCCH_3$) was dissolved in about 4 mL of methylene chloride and carbon monoxide was bubbled through for 3 minutes. The mixture was stirred for 4 hours and treated with CO again and cooled to −15° C. The composition crystallized as yellow needles after 24 hours at −15° C. Solvent was removed using a syringe and the composition was dried under a nitrogen/CO stream. CO may lose easily under reduced pressure affording a copper-acetonitrile adduct. Yield 80%. Mp: about 57° C. (dec.). $^{19}F$ NMR ($CDCl_3$): δ −59.70 (s, 6F, o-$CF_3$), −80.57 (s, 6F, $CF_3$), −106.53 and −110.17 (AB multiplet, J=277.7 Hz, α-CF2), −106.94 and −109.30 (AB multiplet, J=279.3 Hz, α-$CF_2$), −121.72 and −121.79 (s, 2F, o-F), −123.23 and −123.56 (s, 4F, β-$CF_2$). $^1H$ NMR ($CDCl_3$): δ 7.52 to 7.10 (br, 6H, m- and p-Ar), 1.98 (s, 3H, $NCCH_3$). $^1H$ NMR (cyclohexane-$d_{12}$): δ 7.36 to 6.96 (m, 6H, m- and p-Ar), 1.74 (s, 3H, $NCCH_3$). Elemental analysis for $C_{25}H_9F_{22}N_4OCu$: (a) Calculated: C, 34.80; H, 1.05; N, 6.49; (b) Found: C, 33.42; H, 1.04; N, 6.38. IR (KBr, $cm^{-1}$): 2119 (CO).

For synthesis of $[N\{(C_3F_7)C(2-F,6-(CF_3)C_6H_3)N\}_2]CuCO$, THF solution of $[N\{(C_3F_7)C(2-F,6-(CF_3)C_6H_3)N\}_2]H$ (0.420 g, 0.575 mmol) was treated with n-butyllithium (0.25 mL, 2.5M in hexanes) at −60° C. After 2 hours, the mixture warmed slowly to room temperature. Solvent was removed under reduced pressure to obtain a white solid which was dissolved in $CH_2Cl_2$ and added to $(CuOTf)_2$.benzene (0.145 g, 0.287 mmol) in $CH_2Cl_2$ at room temperature. After stirring for 1 hour, the mixture was treated with CO for 5 minutes and stirred for 2 hours. The mixture was filtered through a bed of celite and the filtrate was concentrated using a CO stream. $[N\{(C_3F_7)C(2-F,6-(CF_3)C_6H_3)N\}_2]CuCO$ crystallized as yellow rods from the mixture overnight at 5° C. The composition was dried using a nitrogen stream or may be dried using reduced pressure. Yield 53%. Mp: 65° C. (dec.). $^{19}F$ NMR ($CDCl_3$): δ −59.65 and −59.69 (s, 6F, o-$CF_3$), −80.56 (apparent t, J=−11.5 Hz, 8.6 Hz, 6F, $CF_3$), −106.45 and −110.08 (AB multiplet, J=280.7 Hz, α-$CF_2$), −106.88 and −109.23 (AB multiplet, J=279.3 Hz, α-$CF_2$), −121.60 (br peak with a shoulder, 2F, o-F), −123.21 and −123.52 (s, 4F, β-CF$_2$). $^1$H NMR (CDCl$_3$): δ 7.68-7.10 (m, m,p-Ar). Elemental analysis for C$_{23}$H$_6$F$_{22}$N$_3$OCu: (a) calculated: C, 33.61; H, 0.74; N, 5.11; (b) Found: C, 32.70; H, 0.84; N, 5.12. IR (KBr, cm$^{-1}$):2128 (CO).

When identifying the structure of compositions described herein, a suitable crystal of a sample was covered with a layer of hydrocarbon oil and mounted with paratone-N oil on a cryo-loop, and immediately placed in a low-temperature nitrogen stream. X-ray intensity data were measured at 100 (2) K, on a detector system equipped with a cryostream cooler, a graphite monochromator, and a Mo Kα fine-focus sealed tube (λ=0.710 73 Å). Data (in frames) were integrated with suitable software package available to one of ordinary skill in the art. Data were corrected for absorption effects using a multi-scan technique (SADABS). Structures were solved and refined using a suitable software package available to one of ordinary skill in the art. Additional details of data collection and refinement are provided in TABLES 2-5.

TABLE 2

Crystal data/structure refinement for [N{(C$_3$F$_7$)C(C$_6$F$_5$)N}$_2$]Cu(CO)(CH$_3$CN).

| | |
|---|---|
| Empirical formula | C23 H3 Cu F24 N4 O |
| Formula weight | 870.83 |
| Temperature | 100(2) K |
| Wavelength | 0.71073 Å |
| Crystal system | Monoclinic |
| Space group | P2(1)/c |
| Unit cell dimensions | a = 10.5092(4) Å  α = 90° |
| | b = 12.5716(5) Å  β = 97.5150(10)° |
| | c = 21.8262(9) Å  γ = 90° |
| Volume | 2858.9(2) Å$^3$ |
| Z | 4 |
| Density (calculated) | 2.023 Mg/m$^3$ |
| Absorption coefficient | 0.950 mm$^{-1}$ |
| F(000) | 1688 |
| Crystal size | 0.35 × 0.26 × 0.17 mm$^3$ |
| Theta range for data collection | 2.48 to 28.31° |
| Index ranges | −13 <= h <= 14, −16 <= k <= 16, −29 <= l <= 28 |
| Reflections collected | 26467 |
| Independent reflections | 6973 [R(int) = 0.0166] |
| Completeness to theta = 28.31° | 98.2% |
| Absorption correction | None |
| Max. and min. transmission | 0.8551 and 0.7320 |
| Refinement method | Full-matrix least-squares on F$^2$ |
| Data/restraints/parameters | 6973/0/490 |
| Goodness-of-fit on F$^2$ | 1.060 |
| Final R indices [I > 2sigma(I)] | R1 = 0.0300, wR2 = 0.0812 |
| R indices (all data) | R1 = 0.0322, wR2 = 0.0830 |
| Largest diff. peak and hole | 0.534 and −0.296 e · Å$^{-3}$ |

TABLE 3

Crystal data/structure refinement for [N{(C$_3$F$_7$)C(C$_6$F$_5$)N}$_2$]Cu(C$_2$H$_4$).

| | |
|---|---|
| Empirical formula | C22 H4 Cu F24 N3 |
| Formula weight | 829.82 |
| Temperature | 100(2) K |
| Wavelength | 0.71073 Å |
| Crystal system | Monoclinic |
| Space group | P2(1)/c |
| Unit cell dimensions | a = 11.6782(5) Å  α = 90° |
| | b = 21.1320(8) Å  β = 106.4380 (10)° |
| | c = 11.3774(4) Å  γ = 90° |
| Volume | 2692.99(18) Å$^3$ |
| Z | 4 |
| Density (calculated) | 2.047 Mg/m$^3$ |
| Absorption coefficient | 1.000 mm$^{-1}$ |
| F(000) | 1608 |
| Crystal size | 0.27 × 0.06 × 0.04 mm$^3$ |
| Theta range for data collection | 1.82 to 25.36°. |

TABLE 3-continued

Crystal data/structure refinement for [N{(C$_3$F$_7$)C(C$_6$F$_5$)N}$_2$]Cu(C$_2$H$_4$).

| | |
|---|---|
| Index ranges | −13 <= h <= 14, −25 <= k <= 25, −13 <= l <= 13 |
| Reflections collected | 19960 |
| Independent reflections | 4894 [R(int) = 0.0491] |
| Completeness to theta = 25.36° | 99.1% |
| Absorption correction | None |
| Max. and min. transmission | 0.9659 and 0.7762 |
| Refinement method | Full-matrix least-squares on F$^2$ |
| Data/restraints/parameters | 4894/0/467 |
| Goodness-of-fit on F$^2$ | 1.023 |
| Final R indices [I > 2sigma(I)] | R1 = 0.0376, wR2 = 0.0928 |
| R indices (all data) | R1 = 0.0497, wR2 = 0.0998 |
| Largest diff. peak and hole | 0.649 and −0.485 e · Å$^{-3}$ |

TABLE 4

Crystal data/structure refinement for [N{(C$_3$F$_7$)C(2-F,6-(CF$_3$)C$_6$H$_3$)N}$_2$]Cu(CO)(NCCH$_3$).

| | |
|---|---|
| Empirical formula | C25 H9 Cu F22 N4 O |
| Formula weight | 862.90 |
| Temperature | 100(2) K |
| Wavelength | 0.71073 Å |
| Crystal system | Orthorhombic |
| Space group | Pna2(1) |
| Unit cell dimensions | a = 12.6364(7) Å  α = 90° |
| | b = 10.8052(6) Å  β = 90° |
| | c = 21.8933(12) Å  γ = 90° |
| Volume | 2989.3(3) Å$^3$ |
| Z | 4 |
| Density (calculated) | 1.917 Mg/m$^3$ |
| Absorption coefficient | 0.899 mm$^{-1}$ |
| F(000) | 1688 |
| Crystal size | 0.48 × 0.41 × 0.36 mm$^3$ |
| Theta range for data collection | 2.10 to 25.98°. |
| Index ranges | −15 <= h <= 15, −13 <= k <= 13, −26 <= l <= 27 |
| Reflections collected | 21561 |
| Independent reflections | 5843 [R(int) = 0.0473] |
| Completeness to theta = 25.98° | 100.0% |
| Absorption correction | None |
| Max. and min. transmission | 0.7379 and 0.6722 |
| Refinement method | Full-matrix least-squares on F$^2$ |
| Data/restraints/parameters | 5843/22/407 |
| Goodness-of-fit on F$^2$ | 1.056 |
| Final R indices [I > 2sigma(I)] | R1 = 0.0418, wR2 = 0.1023 |
| R indices (all data) | R1 = 0.0469, wR2 = 0.1062 |
| Absolute structure parameter | 0.57(2) |
| Largest diff. peak and hole | 0.506 and −0.398 e · Å$^{-3}$ |

TABLE 5

Crystal data/structure refinement for [N{(C$_3$F$_7$)C(2-F,6-(CF$_3$)C$_6$H$_3$)N}$_2$]CUCO.

| | |
|---|---|
| Empirical formula | C23 H6 Cu F22 N3 O |
| Formula weight | 821.85 |
| Temperature | 100(2) K |
| Wavelength | 0.71073 Å |
| Crystal system | Monoclinic |
| Space group | P2(1)/n |
| Unit cell dimensions | a = 24.6256(16) Å  α = 90° |
| | b = 9.7507(6) Å  β = 113.2780(10)° |
| | c = 25.1455(16) Å  γ = 90° |
| Volume | 5546.4(6) Å$^3$ |
| Z | 8 |
| Density (calculated) | 1.968 Mg/m$^3$ |
| Absorption coefficient | 0.962 mm$^{-1}$ |

TABLE 5-continued

Crystal data/structure refinement for
[N{(C₃F₇)C(2-F,6-(CF₃)C₆H₃)N}₂]CUCO.

| | |
|---|---|
| F(000) | 3200 |
| Crystal size | 0.26 × 0.19 × 0.04 mm³ |
| Theta range for data collection | 1.96 to 25.50°. |
| Index ranges | −29 <= h <= 29, −11 <= k <= 11, −30 <= l <= 30 |
| Reflections collected | 40342 |
| Independent reflections | 10323 [R(int) = 0.0508] |
| Completeness to theta = 25.50° | 99.9% |
| Absorption correction | None |
| Max. and min. transmission | 0.9625 and 0.7893 |
| Refinement method | Full-matrix least-squares on F² |
| Data/restraints/parameters | 10323/0/901 |
| Goodness-of-fit on F² | 1.023 |
| Final RXZ indices [I > 2sigma(I)] | R1 = 0.0556, wR2 = 0.1461 |
| R indices (all data) | R1 = 0.0776, wR2 = 0.1626 |
| Absolute structure parameter | 0.57(2) |
| Largest diff. peak and hole | 1.770 and −0.673 e · Å⁻³ |

For [N{(C₃F₇)C(C₆F₅)N}₂]Cu(CO)(CH₃CN) and [N{(C₃F₇)C(C₆F₅)N}₂]Cu(C₂H₄), hydrogen atoms of acetonitrile and ethylene units were located from a difference map and included/refined isotropically. All non-hydrogen atoms were refined anisotropically.

[N{(C₃F₇)C(2-F,6-(CF₃)C₆H₃)N}₂]Cu(CO)(NCCH₃) crystallized in the Pna2(1) space group. One of the aryl groups was disordered over two positions. The ortho-CF₃ group in about 65% of the molecules occupied the carbonyl group side, whereas in the remaining portion of the molecule (about 35%), it occupied the acetonitrile group side. Carbon and fluorine atoms of the disordered aryl ring were refined isotropically. All remaining non-hydrogen atoms were refined anisotropically. Hydrogen atoms were placed at calculated positions and refined using a riding model. The crystals show racemic twinning; refined using suitable commands.

[N{(C₃F₇)C(2-F,6-(CF₃)C₆H₃)N}₂]CuCO crystallized in the P2₁/n space group. Crystallization, two chemically similar but crystallographically different molecules were found in the asymmetric unit (FIG. 10C). There was minor disorder in few fluorine atom positions of the C₃F₇ moieties as indicated by residual peaks. All non-hydrogen atoms were refined anisotropically. Hydrogen atoms were placed at calculated positions and refined using a riding model.

Figure 11:
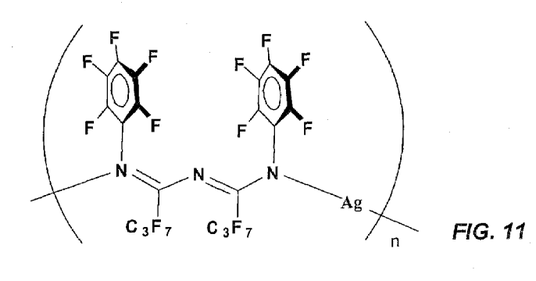
FIG. 11 depicts a representative structure of a fully-fluorinated triazapentadienyl silver(I) complex described herein.

Compounds described herein may coordinate with any of a number of metal ions, such as but not limited to silver (Ag), copper, gold, thallium, and alkali metals. An example of a fluorinated triazapentadienyl silver(I) complex described herein is depicted in FIG. 11. Additional examples include [N{(C₃F₂)C(2-F,6-CF₃C₆H₃)N}₂]Ag and [N{(C₃F₂)C(2,6-Cl₂C₆H₃)N}₂]Ag.

Reactions for complexation with silver(I) were performed in light-protected flasks. For synthesis of {[N{(C₃F₇)C(C₆F₅)N}₂]Ag}ₙ (FIG. 11), [N{(C₃F₇)C(C₆F₅)N}₂]H (1.0 g, 1.35 mmol), silver(I) oxide (0.19 g, 0.81 mmol) and THF (40 μL) were heated at 70° C. in an oil bath for 12 hours followed by filtering over a bed of diatomite. Solvent was evaporated to dryness to yield the product as a white solid. It was recrystallized from a mixture of acetone-toluene by slow evaporation to obtain transparent crystals as thin squares. Yield: 60%. Mp: 140-150° C. (dec). ¹⁹F NMR (DMSO-d₆): δ −79.9 (apparent triplet, J=8.7 Hz, 6F, CF₃), −113.3 (s, 4F, α-CF₂), −125.3 (s, 4F, β-CF₂), −149.0 (d, J=19.5 Hz, 4F, o-Ar), −166.3 (t, J=21.7 Hz, 19.5 Hz, 4F, m-Ar), −167.4 (t, J=23.8 Hz, 21.7 Hz, 2F, p-Ar). Elemental analysis for C₂₀F₂₄N₃Ag: (a) Calculated: C, 28.39; H, 0.00; N, 4.97; (b) Found: C, 28.28; H, <0.20; N, 5.20.

The new class of fluorinated triazapentadiene compounds with and without metal complexation as described herein were analyzed for antibacterial activity against several bacterial strains (both Gram positive and Gram negative). Methods for antimicrobial analysis included a modified Kirby-Bauer method and a determination of their minimum inhibitory concentrations. In brief, the modified Kirby-Bauer method relied on placement of a filter disk impregnated with a desired compound on a solid growth medium. Bacteria were grown to a confluent lawn and the extent of growth inhibition was measured (e.g., as an extent/percentage of a clear zone on the disk and/or solid medium). The assessment of minimum inhibitory concentration (MIC) was determined by a lowest concentration that visibly inhibited growth of bacteria in culture.

Filter disks were provided as sterile filter paper (about 6 mm in diameter) and spotted with 20 μL of a selected compound. Each compound was initially dissolved in dimethyl-sulfoxide (DMSO); any subsequent dilutions were also made in DMSO. Each filter was placed on an LB agar plate spread with 100 μL of a bacterial culture that had been grown overnight in suitable LB broth. Plates were incubated overnight at 37° C., after which, the extent of growth inhibition around each filter disk was measured. Bacterial strains included *Staphylococcus aureus* (ATCC 25923), *Pseudomonas aeruginosa* PAO1, *Bacillus subtilis* W168 and *Escherichia coli* HB101. The former two strains are pathogenic Gram-positive and Gram-negative bacteria, respectively. The latter two strains are non-pathogenic Gram-positive and Gram-negative bacterial strains, respectively.

For MIC assessment, compounds were initially dissolved in DMSO and serial dilutions of soluble compounds were made in LB broth. 4 μL of a 37° C. overnight LB broth culture was inoculated into 2 mL of each dilution in LB (each MIC was eventually bracketed to within two fold up and down of that concentration) and the cultures were incubated overnight (with rapid shaking at 37° C.) before being evaluated for growth or lack thereof visually.

Antimicrobial activity of various compounds described herein are depicted in TABLES 6-15. For the TABLES, the concentrations (μg/ml) were normalized to approximately equal molar concentrations for each row and for each compound. The FW for each compound is: [N{(C₃F₇)C(C₆F₅)N}₂]Ag (FW 846.06); [N{(C₃F₇)C(C₆F₅)N}₂]H(FW 739.20); [N{(C₃F₇)C(2-F,6-(CF₃)C₆H₃)N}₂]H(FW 731.28); [N{(C₃F₇)C(C₆H₅)N}₂]H(FW 559.30); [N{(C₃F₇)C(Mes)N}₂]H(FW 643.46); [N{(C₃F₇)C(2,6-Cl₂C₆H₃)N}₂]H(FW 697.08); [N{(CF₃)C(C₆F₅)N}₂]H(FW 697.08); [N{(C₃F₇)C(2-F,6-CF₃C₆H₃)N}₂]Ag (FW 838.15); [N{(C₃F₇)C(2,6-Cl₂C₆H₃)N}₂]Ag (FW 803.94); AgNO₃ (FW 169.9); silver (I) sulfadiazine (FW 357.14). In the tables, NZ is no zone of inhibition and ND is not determined.

TABLE 6

Disk sensitivity test with [N{(C₃F₇)C(C₆F₅)N}₂]Ag

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $4.86 \times 10^4$ | $5.7 \times 10^1$ | 70.0 | 47.0 | 27.0 | 18.0 |
| $4.86 \times 10^3$ | $5.7 \times 10^0$ | 33.0 | 37.0 | 16.5 | 14.0 |
| $4.86 \times 10^2$ | $5.7 \times 10^{-1}$ | 39.0 | 38.0 | 12.0 | 11.0 |
| $4.86 \times 10^1$ | $5.7 \times 10^{-2}$ | 21.5 | 22.0 | 8.0 | 8.5 |
| $4.86 \times 10^0$ | $5.7 \times 10^{-3}$ | 10.0 | 11.0 | 7.5 | 8.0 |
| $4.86 \times 10^{-1}$ | $5.7 \times 10^{-4}$ | 6.0 (NZ)[b] | 7.5 | 6.0 (NZ) | 6.0 (NZ) |
| $4.86 \times 10^{-2}$ | $5.7 \times 10^{-5}$ | 6.0 (NZ) | 6.0 (NZ) | 6.0 (NZ) | 6.0 (NZ) |
| $4.86 \times 10^{-3}$ | $5.7 \times 10^{-6}$ | 6.0 (NZ) | 6.0 (NZ) | 6.0 (NZ) | 6.0 (NZ) |

TABLE 7

Disk sensitivity test with [N{(C₃F₇)C(C₆F₅)N}₂]H

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $4.20 \times 10^4$ | $5.7 \times 10^1$ | 75.0 | 71.0 | 9.0 | 9.5 |
| $4.20 \times 10^3$ | $5.7 \times 10^0$ | 37.5 | 39.0 | 8.0 | 9.0 |
| $4.20 \times 10^2$ | $5.7 \times 10^{-1}$ | 40.0 | 47.0 | 8.0 | 9.0 |
| $4.20 \times 10^1$ | $5.7 \times 10^{-2}$ | 19.0 | 22.0 | 8.0 | 8.5 |
| $4.20 \times 10^0$ | $5.7 \times 10^{-3}$ | 9.0 | 10.0 | 7.0 | 7.0 |
| $4.20 \times 10^{-1}$ | $5.7 \times 10^{-4}$ | 6.0 (NZ) | 8.0 | ND[c] | ND |
| $4.20 \times 10^{-2}$ | $5.7 \times 10^{-5}$ | 6.0 (NZ) | 6.0 (NZ) | ND | ND |
| $4.20 \times 10^{-3}$ | $5.7 \times 10^{-6}$ | 6.0 (NZ) | 6.0 (NZ) | ND | ND |
| $4.20 \times 10^{-4}$ | $5.7 \times 10^{-7}$ | 6.0 (NZ) | 6.0 (NZ) | ND | ND |

TABLE 8

Disk sensitivity test with [N{(CF₃)C(C₆F₅)N}₂]H

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $3.10 \times 10^4$ | $5.8 \times 10^1$ | 36.5 | 45.0 | 10.0 | 11.0 |
| $3.10 \times 10^3$ | $5.8 \times 10^0$ | 35.0 | 33.0 | 9.0 | 10.0 |
| $3.10 \times 10^2$ | $5.8 \times 10^{-1}$ | 30.0 | 31.0 | 9.5 | 9.0 |
| $3.10 \times 10^1$ | $5.8 \times 10^{-2}$ | 13.0 | 22.0 | 9.5 | 8.0 |
| $3.10 \times 10^0$ | $5.8 \times 10^{-3}$ | 22.0 | 8.0 | 9.0 | 8.5 |
| $3.10 \times 10^{-1}$ | $5.8 \times 10^{-4}$ | 9.0 | 7.5 | ND | ND |
| $3.10 \times 10^{-2}$ | $5.8 \times 10^{-5}$ | ND | 6.0 (NZ) | ND | ND |
| $3.10 \times 10^{-3}$ | $5.8 \times 10^{-6}$ | ND | 6.0 (NZ) | ND | ND |

TABLE 9

Disk sensitivity test with [N{(C₃F₇)C(2-F,6-CF₃C₆H₃)N}₂]Ag

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $4.81 \times 10^4$ | $5.7 \times 10^1$ | 19.0 | 115.0 | 23.5 | 22.0 |
| $4.81 \times 10^3$ | $5.7 \times 10^0$ | 14.0 | 131.0 | 15.0 | 12.5 |
| $4.81 \times 10^2$ | $5.7 \times 10^{-1}$ | 9.5 | 78.0 | 9.0 | 10.0 |
| $4.81 \times 10^1$ | $5.7 \times 10^{-2}$ | 9.0 | 39.0 | 6.0 (NZ) | 9.0 |
| $4.81 \times 10^0$ | $5.7 \times 10^{-3}$ | 7.5 | 10.0 | 6.0 (NZ) | 8.0 |
| $4.81 \times 10^{-1}$ | $5.7 \times 10^{-4}$ | 6.0 (NZ) | 10.0 | ND[b] | ND |
| $4.81 \times 10^{-2}$ | $5.7 \times 10^{-5}$ | 6.0 (NZ) | 9.0 | ND | ND |
| $4.81 \times 10^{-3}$ | $5.7 \times 10^{-6}$ | 6.0 (NZ) | 9.0 | ND | ND |
| $4.81 \times 10^{-4}$ | $5.7 \times 10^{-7}$ | 6.0 (NZ) | 7.5 | ND | ND |

TABLE 10

Disk sensitivity test with [N{(C$_3$F$_7$)C(2-F,6-(CF$_3$)C$_6$H$_3$)N}$_2$]H

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $4.20 \times 10^4$ | $5.7 \times 10^1$ | 47.5 | 100.0 | 9.0 | 9.0 |
| $4.20 \times 10^3$ | $5.7 \times 10^0$ | 36.0 | 85.0 | 8.5 | 8.5 |
| $4.20 \times 10^2$ | $5.7 \times 10^{-1}$ | 34.0 | 50.0 | 8.0 | 8.0 |
| $4.20 \times 10^1$ | $5.7 \times 10^{-2}$ | 9.0 | 30.0 | 8.0 | 7.0 |
| $4.20 \times 10^0$ | $5.7 \times 10^{-3}$ | 8.0 | 13.5 | 8.0 | 7.0 |
| $4.20 \times 10^{-1}$ | $5.7 \times 10^{-4}$ | 6.0 (NZ) | 7.0 | 7.0 | 7.0 |
| $4.20 \times 10^{-2}$ | $5.7 \times 10^{-5}$ | 6.0 (NZ) | 8.0 | 6.0 (NZ) | 7.0 |
| $4.20 \times 10^{-3}$ | $5.7 \times 10^{-6}$ | ND | 8.0 | ND | ND |
| $4.20 \times 10^{-4}$ | $5.7 \times 10^{-7}$ | ND | 7.5 | ND | ND |

TABLE 11

Disk sensitivity test with [N{(C$_3$F$_7$)C(2,6-Cl$_2$C$_6$H$_3$)N}$_2$]Ag

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $4.62 \times 10^4$ | $5.7 \times 10^1$ | 20.0 | 19.5 | 15.0 | 15.5 |
| $4.62 \times 10^3$ | $5.7 \times 10^0$ | 16.5 | 21.0 | 13.5 | 16.0 |
| $4.62 \times 10^2$ | $5.7 \times 10^{-1}$ | 15.0 | 18.0 | 10.0 | 11.0 |
| $4.62 \times 10^1$ | $5.7 \times 10^{-2}$ | 14.5 | 19.0 | 7.0 | 9.0 |
| $4.62 \times 10^0$ | $5.7 \times 10^{-3}$ | 11.0 | 12.0 | 6.0 (NZ) | 7.0 |
| $4.62 \times 10^{-1}$ | $5.7 \times 10^{-4}$ | 6.0 (NZ) | 6.0 (NZ) | ND | ND |
| $4.62 \times 10^{-2}$ | $5.7 \times 10^{-5}$ | 6.0 (NZ) | 6.0 (NZ) | ND | ND |

TABLE 12

Disk sensitivity test with [N{(C$_3$F$_7$)C(2,6-Cl$_2$C$_6$H$_3$)N}$_2$]H

| Concentration (μg/ml)[a] | Concentration (mM) | Diameter of the zone of growth inhibition (mm) | | | |
|---|---|---|---|---|---|
| | | S. aureus | B. subtilis | P. aeruginosa | E. coli |
| $4.00 \times 10^4$ | $5.7 \times 10^1$ | 13.0 | 21.0 | 9.0 | 9.0 |
| $4.00 \times 10^3$ | $5.7 \times 10^0$ | 20.0 | 19.0 | 8.0 | 8.0 |
| $4.00 \times 10^2$ | $5.7 \times 10^{-1}$ | 16.0 | 18.5 | 8.0 | 8.0 |
| $4.00 \times 10^1$ | $5.7 \times 10^{-2}$ | 15.0 | 19.0 | 8.0 | 8.0 |
| $4.00 \times 10^0$ | $5.7 \times 10^{-3}$ | 7.0 | 13.0 | 7.0 | 6.0 (NZ) |
| $4.00 \times 10^{-1}$ | $5.7 \times 10^{-4}$ | 7.0 | 8.5 | ND | ND |
| $4.00 \times 10^{-2}$ | $5.7 \times 10^{-5}$ | 8.0 | 7.0 | ND | ND |
| $4.00 \times 10^{-3}$ | $5.7 \times 10^{-6}$ | 6.0 (NZ) | 7.5 | ND | ND |
| $4.00 \times 10^{-4}$ | $5.7 \times 10^{-7}$ | 6.0 (NZ) | 6.0 (NZ) | ND | ND |

TABLE 13

Disk sensitivity test with [N{(C$_3$F$_7$)C(Mes)N}$_2$]H

| Concentration (μg/ml) | Concentration (mM) | Diameter of the zone of growth inhibition (mm) | | | |
|---|---|---|---|---|---|
| | | S. aureus | B. subtilis | P. aeruginosa | E. coli |
| $3.69 \times 10^4$ | $5.7 \times 10^1$ | 9.5 | 9.0 | 9.0 | 10.0 |
| $3.69 \times 10^3$ | $5.7 \times 10^0$ | 7.5 | 8.0 | 8.5 | 8.0 |
| $3.69 \times 10^2$ | $5.7 \times 10^{-1}$ | 6.0 (NZ) | 6.0 (NZ) | 7.5 | 7.5 |
| $3.69 \times 10^1$ | $5.7 \times 10^{-2}$ | 6.0 (NZ) | 6.0 (NZ) | 7.5 | 7.0 |
| $3.69 \times 10^0$ | $5.7 \times 10^{-3}$ | 6.0 (NZ) | 6.0 (NZ) | 7.0 | 7.0 |

TABLE 14

Disk sensitivity test with AgNO$_3$

| Concentration (µg/ml) | Concentration (mM) | Diameter of the zone of growth inhibition (mm) | | | |
|---|---|---|---|---|---|
| | | S. aureus | B. subtilis | P. aeruginosa | E. coli |
| $1.00 \times 10^4$ | $5.9 \times 10^{-2}$ | 10.5 | 16.0 | 16.0 | 15.0 |
| $1.00 \times 10^3$ | $5.9 \times 10^{-3}$ | 9.0 | 13.0 | 12.5 | 14.0 |
| $1.00 \times 10^2$ | $5.9 \times 10^{-4}$ | 8.5 | 13.0 | 9.5 | 13.0 |
| $1.00 \times 10^1$ | $5.9 \times 10^{-5}$ | 7.0 | 9.5 | 6.0 (NZ) | 8.5 |
| $1.00 \times 10^0$ | $5.9 \times 10^{-6}$ | 6.0 (NZ) | 9.0 | 6.0 (NZ) | 7.0 |

TABLE 15

Disk sensitivity test with Silver(I) sulfadiazine

| Concentration (µg/ml)$^a$ | Concentration (mM) | Diameter of the zone of growth inhibition (mm) | | | |
|---|---|---|---|---|---|
| | | S. aureus | B. subtilis | P. aeruginosa | E. coli |
| $2.05 \times 10^4$ | $5.7 \times 10^{-2}$ | 12.5 | 12.5 | 17.0 | 15.0 |
| $2.05 \times 10^3$ | $5.7 \times 10^{-3}$ | 11.0 | 12.0 | 15.0 | 11.5 |
| $2.05 \times 10^2$ | $5.7 \times 10^{-4}$ | 9.5 | 9.5 | 7.0 | 6.0 (NZ) |
| $2.05 \times 10^1$ | $5.7 \times 10^{-5}$ | 8.0 | 9.0 | 7.0 | 6.0 (NZ) |
| $2.05 \times 10^0$ | $5.7 \times 10^{-6}$ | 6.0 (NZ) | 6.0 (NZ) | ND | ND |

For antibacterial assessment, DMSO, as a control, was used and a no zone of inhibition was observed for all compounds described herein. Other comparative compounds used were representative conventional compounds currently in use for antibacterial purposes and included AgNO$_3$ and silver(I) sulfadiazine.

Compounds described herein show remarkably high antimicrobial activity as further evidenced in TABLES 16-18. In TABLES 16-18, the last column reflects antimicrobial efficacy of each compound relative to AgNO$_3$, wherein efficacy is assessed on a per mole basis in a comparison with the MIC values. Effective compounds as antimicrobials include the highly fluorinated triazapentadiene [N{(CF$_3$)C(C$_6$F$_5$)N}$_2$]H and [N{(C$_3$F$_7$)C(C$_6$F$_5$)N}$_2$]H and the silver adduct [N{(C$_3$F$_7$)C(C$_6$F$_5$)N}$_2$]Ag; the fluorinated [N{(C$_3$F$_7$)C(2-F,6-(CF$_3$)C$_6$H$_3$)N}$_2$]H and its silver adduct [N{(C$_3$F$_7$)C(2-F,6-CF$_3$C$_6$H$_3$)N}$_2$]Ag; and the chlorinated compound [N{(C$_3$F$_7$)C(2,6-Cl$_2$Ph)N}$_2$]H and its silver adduct [N{(C$_3$F$_7$)C(2,6-Cl$_2$C$_6$H$_3$)N}$_2$]Ag.

TABLE 16

S. aureus.

| Compound | MIC (µg/ml) | MIC (mM) | Relative to AgNO$_3$ |
|---|---|---|---|
| [N{(C$_3$F$_7$)C(C$_6$F$_5$)N}$_2$]Ag | 1.80 | $2.13 \times 10^{-3}$ | 34.45 |
| [N{(C$_3$F$_7$)C(C$_6$F$_5$)N}$_2$]H | 1.57 | $2.12 \times 10^{-3}$ | 34.71 |
| [N{(CF$_3$)C(C$_6$F$_5$)N}$_2$]H | 1.46 | $2.71 \times 10^{-3}$ | 27.16 |
| [N{(C$_3$F$_7$)C(2-F,6-CF$_3$C$_6$H$_3$)N}$_2$]Ag | $8.78 \times 10^{-1}$ | $1.05 \times 10^{-3}$ | 70.10 |
| [N{(C$_3$F$_7$)C(2-F,6-(CF$_3$)C$_6$H$_3$)N}$_2$]H | 1.55 | $1.06 \times 10^{-3}$ | 34.71 |
| [N{(C$_3$F$_7$)C(2,6-Cl$_2$C$_6$H$_3$)N}$_2$]Ag | 0.853 | $1.12 \times 10^{-2}$ | 69.43 |
| [N{(C$_3$F$_7$)C(2,6-Cl$_2$C$_6$H$_3$)N}$_2$]H | 7.80 | $2.12 \times 10^{-3}$ | 6.57 |
| [N{(C$_3$F$_7$)C(Mes)N}$_2$]H | 2252.38 | 3.50 | $2.10 \times 10^{-2}$ |
| AgNO$_3$ | 12.50 | $7.36 \times 10^{-2}$ | 1.00 |
| silver(I) sulfadiazine | 16.00 | $4.48 \times 10^{-2}$ | 1.64 |

TABLE 17

B. subtilis.

| Compound | MIC (µg/ml) | MIC (mM) | Relative to AgNO$_3$ |
|---|---|---|---|
| [N{(C$_3$F$_7$)C(C$_6$F$_5$)N}$_2$]Ag | 1.80 | $2.13 \times 10^{-3}$ | 69.01 |
| [N{(C$_3$F$_7$)C(C$_6$F$_5$)N}$_2$]H | 1.57 | $2.12 \times 10^{-3}$ | 69.34 |
| [N{(CF$_3$)C(C$_6$F$_5$)N}$_2$]H | $7.29 \times 10^{-1}$ | $1.35 \times 10^{-3}$ | 108.89 |
| [N{(C$_3$F$_7$)C(2-F,6-CF$_3$C$_6$H$_3$)N}$_2$]Ag | $8.70 \times 10^{-2}$ | $1.04 \times 10^{-4}$ | 1413.46 |
| [N{(C$_3$F$_7$)C(2-F,6-(CF$_3$)C$_6$H$_3$)N}$_2$]H | $1.60 \times 10^{-1}$ | $2.19 \times 10^{-4}$ | 671.23 |
| [N{(C$_3$F$_7$)C(2,6-Cl$_2$C$_6$H$_3$)N}$_2$]Ag | $4.27 \times 10^{-1}$ | $5.31 \times 10^{-4}$ | 276.84 |
| [N{(C$_3$F$_7$)C(2,6-Cl$_2$C$_6$H$_3$)N}$_2$]H | $4.27 \times 10^{-1}$ | $4.59 \times 10^{-4}$ | 320.26 |
| [N{(C$_3$F$_7$)C(Mes)N}$_2$]H | 1732.64 | 2.69 | $5.46 \times 10^{-2}$ |
| AgNO$_3$ | 25.00 | $1.47 \times 10^{-1}$ | 1.00 |
| silver(I) sulfadiazine | 89.18 | $2.50 \times 10^{-1}$ | $5.88 \times 10^{-1}$ |

TABLE 18

P. aeruginosa.

| Compound | MIC (µg/ml) | MIC (mM) | Relative to AgNO$_3$ |
|---|---|---|---|
| [N{(C$_3$F$_7$)C(C$_6$F$_5$)N}$_2$]Ag | 23.69 | $2.80 \times 10^{-2}$ | $6.57 \times 10^{-1}$ |
| [N{(C$_3$F$_7$)C(C$_6$F$_5$)N}$_2$]H | 2643.48 | 3.58 | $5.14 \times 10^{-3}$ |
| [N{(CF$_3$)C(C$_6$F$_5$)N}$_2$]H | 1586.90 | 2.94 | $6.26 \times 10^{-3}$ |
| [N{(C$_3$F$_7$)C(2-F,6-CF$_3$C$_6$H$_3$)N}$_2$]Ag | 17.56 | $2.1 \times 10^{-2}$ | $8.76 \times 10^{-1}$ |
| [N{(C$_3$F$_7$)C(2-F,6-(CF$_3$)C$_6$H$_3$)N}$_2$]H | 2912.70 | 3.98 | $4.62 \times 10^{-3}$ |
| [N{(C$_3$F$_7$)C(2,6-Cl$_2$C$_6$H$_3$)N}$_2$]Ag | 72.20 | $8.98 \times 10^{-2}$ | $2.05 \times 10^{-1}$ |
| [N{(C$_3$F$_7$)C(2,6-Cl$_2$C$_6$H$_3$)N}$_2$]H | >16671.80 | >23.92 | $<7.69 \times 10^{-4}$ |
| [N{(C$_3$F$_7$)C(Mes)N}$_2$]H | 1402.43 | 2.18 | $8.44 \times 10^{-3}$ |
| AgNO$_3$ | 3.12 | $1.84 \times 10^{-2}$ | 1.00 |
| silver(I) sulfadiazine | 2.00 | $5.60 \times 10^{-3}$ | 3.29 |

TABLE 19

*E. coli.*

| Compound | MIC (μg/ml) | MIC (mM) | Relative to AgNO$_3$ |
|---|---|---|---|
| [N{(C$_3$F$_7$)C(C$_6$F$_5$)N}$_2$]Ag | 23.69 | 2.80 × 10$^{-2}$ | 2.10 |
| [N{(C$_3$F$_7$)C(C$_6$F$_5$)N}$_2$]H | 2643.48 | 3.58 | 1.65 × 10$^{-2}$ |
| [N{(CF$_3$)C(C$_6$F$_5$)N}$_2$]H | 396.73 | 1.10 | 5.35 × 10$^{-2}$ |
| [N{(C$_3$F$_7$)C(2-F,6-CF$_3$C$_6$H$_3$)N}$_2$]Ag | 8.78 | 1.00 × 10$^{-2}$ | 5.89 |
| [N{(C$_3$F$_7$)C(2-F,6-(CF$_3$)C$_6$H$_3$)N}$_2$]H | 2912.70 | 3.98 | 1.48 × 10$^{-2}$ |
| [N{(C$_3$F$_7$)C(2,6-Cl$_2$C$_6$H$_3$)N}$_2$]Ag | 72.20 | 8.98 × 10$^{-2}$ | 6.56 × 10$^{-1}$ |
| [N{(C$_3$F$_7$)C(2,6-Cl$_2$C$_6$H$_3$)N}$_2$]H | >16671.80 | >23.92 | <2.46 × 10$^{-3}$ |
| [N{(C$_3$F$_7$)C(Mes)N}$_2$]H | 1126.88 | 1.75 | 3.37 × 10$^{-2}$ |
| AgNO$_3$ | 10.0 | 5.89 × 10$^{-2}$ | 1.00 |
| silver(I) sulfadiazine | 12.81 | 3.59 × 10$^{-2}$ | 1.64 |

TABLES 6-19 illustrate that compounds herein are highly effective at inhibiting growth of Gram-positive bacteria (e.g., *S. aureus* and *B. subtilis*) and serve as suitable antibacterial agents for use, such as medicinal use and/or as an antibacterial additive, due to their thermal stability. Compositions herein were 27-1,400 times more effective than AgNO$_3$ and approximately 16-2,400 times more effective than a currently used antimicrobial, silver sulfadiazine (TABLES 16-19). The Gram-negative bacteria *P. aeruginosa* (an opportunistic pathogen) and *E. coli* (strains of which are pathogenic) were most sensitive to ([N{(C$_3$F$_7$)C(C$_6$F$_5$)N}$_2$]Ag, [N{(C$_3$F$_7$)C(2-F,6-CF$_3$C$_6$H$_3$)N}$_2$]Ag and [N{(C$_3$F$_7$)C(2,6-Cl$_2$C$_6$H$_3$)N}$_2$]Ag at relatively equivalent levels.

An additional finding suggests that presence of a halogen on phenyl groups in the triazapentadienes compositions herein may be important for improving antibacterial activity against Gram-positive organisms (e.g., *S. aureus* and *B. subtilis*) because [N{(C$_3$F$_7$)C(Mes)N}$_2$]H was less effective than other triazapentadienes not containing a halogen on its phenyl groups.

In one or more forms, effective amounts of any one or a number of compositions described herein are provided in an appropriate diluent with or without additional ingredients and provided as an antimicrobial solution. The solution may be provided in a concentrated form and further diluted at a later stage, wherein dilutions were at any concentration desired and may depend on preference and/or suitable effectiveness. In addition, the solution may be provided with a pharmaceutical carrier for medicament purposes. In addition or as an alternative, one or more compositions herein may be provided in an effective amount on a surface to act as a surface repellant/antimicrobial.

An agent may remain in a concentrated form or be provided at its effective amount, which, in some forms, may depend on the microbe of interest. For example, as an antimicrobial agent against certain Gram positive bacteria, a composition such as [N{(C$_3$F$_7$)C(C$_6$F$_5$)N}$_2$]Ag or [N{(C$_3$F$_7$)C(C$_6$F$_5$)N}$_2$]H or [N{(CF$_3$)C(C$_6$H$_5$)N}$_2$]H may (alone or in combination) be provided at a concentration of about or greater than 5.0×10$^{-4}$ mM and provided at a concentration of about or greater than 5.0×10$^{-3}$ mM when used against certain Gram negative bacteria (see, e.g., TABLES 6, 7 or 8, respectively). An antimicrobial agent such as [N{(C$_3$F$_7$)C(2-F,6-CF$_3$C$_6$H$_3$)N}$_2$]Ag or N{(C$_3$F$_7$)C(2-F,6-(CF$_3$)C$_6$H$_3$)N}$_2$]H may be provided at a concentration of about or greater than 5.0×10$^{-7}$ mM against certain Gram positive bacteria and at a concentration of about or greater than 5.0×10$^{-3}$ mM when provided against other Gram negative bacteria (see, e.g., TABLES 9 or 10, respectively). An antimicrobial agent such as [N{(C$_3$F$_7$)C(2,6-Cl$_2$C$_6$H$_3$)N}$_2$]Ag may be provided at a concentration of about or greater than 5.0×10$^{-3}$ mM when provided against certain Gram positive and/or Gram negative bacteria (see, e.g., TABLE 11). An antimicrobial agent such as [N{(C$_3$F$_7$)C(2,6-Cl$_2$C$_6$H$_3$)N}$_2$]H may be provided at a concentration of about or greater than 5.0×10$^{-6}$ mM against certain Gram positive bacteria and at a concentration of about or greater than 5.0×10$^{-3}$ mM when provided against Gram negative bacteria (see, e.g., TABLE 12). An antimicrobial agent such as [N{(C$_3$F$_7$)C(Mes)N}$_2$]H may be provided at a concentration of about or greater than 5.0 mM against certain Gram positive bacteria and at a concentration of about or greater than 5.0×10$^{-3}$ mM when provided against Gram negative bacteria (see, e.g., TABLE 13). Effective antibacterial concentrations are similar for many compositions described herein.

When in solution a water dispersible component is typically included. This is preferably a water soluble solvent, such as dimethylsulfoxide, toluene, tetrahydrofuran, dichloromethane, diethyl ether, and hexane. In addition or as alternatives, solvents may include polyethylene glycol 400, hexylene glycol, propylene glycol, polypropylene glycol-10 methylglucose ether, ethoxydiglycol, polyethylene glycol-6 caprylic/capric glyceride, ethylene glycol monobutyl ether, polyethylene glycol-8 caprylic/capric glycerides, 3-methoxy-3-methyl-1-butanol, dimethyl isosorbide and mixtures thereof, as examples.

A formulation of compositions described herein in a solution or pharmaceutical preparations is routine. In one embodiment, a common administration vehicle (e.g., tablet, implants, injectable solution, injectable liposome solution, etc.) will contain at least one compound described herein and other suitable ingredients. Other suitable ingredients may include stabilizing agents (e.g., carriers known in the art such as albumin, a globulin, a gelatin, a protamine or a salt of protamine), immunosuppressive agents (e.g., prednisone, melphalain, prednisolone, cyclophosphamide, cyclosporine, 6-mercaptopurine, methotrexate, azathioprine and i.v. gamma globulin and suitable combinations), tolerance-inducing agents, potentiators (e.g., monensin, ammonium chloride, perhexyline, verapamil, amantadine and chloroquine) and/or side-effect relieving agents, as examples. All of such additives when provided for human use have known efficacious dose ranges, such as disclosed in the Physician's Desk Reference, 41st Ed., Publisher Edward R. Barnhart, N. J. (1987).

As such, poly-halogenated 1,3,5-triazapetadienes are useful ligands for other compounds, including metals and carbon- or nitrogen-based donor molecule. Such compounds (with and without metal complexation) are potent antibacterial compounds. Such compounds as described herein provide for disinfectant, antiseptic and/or antimicrobial use for personal, medical, commercial and/or industrial applications. The improved compounds as described are also suitable as ligands for metal coordination chemistry. As described, resulting metal adducts may also serve as active catalysts for one or more chemical processes.

While specific alternatives to steps of the invention have been described herein, additional alternatives not specifically disclosed but known in the art are intended to fall within the scope of the invention. Thus, it is understood that other applications of the present invention will be apparent to those skilled in the art upon reading the described embodiment and after consideration of the appended claims and drawing.

What is claimed is:

1. A method comprising:

wherein $R^1$ is an alkyl or aryl group and $R^2$ is a fluoro alkyl group.

2. The method of claim 1, wherein $R^1$ is selected from the group consisting of $C_6F_5$, 2-F,6-$(CF_3)C_6H_3$, 3,5-$(CF_3)_2C_6H_3$ and 2,6-$Cl_2C_6H_3$.

3. The method of claim 1, wherein $R^2$ is $CF_3$ or $C_3F_7$.

4. The method of claim 1, wherein, $R^2$ is $C_3F_7$, and wherein the method further comprises reacting $C_6F_5NH_2$, $C_3F_7$—CF=N—$C_4F_9$ and triethylamine in a molar ratio at or about 2:1:3.

5. The method of claim 1, wherein, $R^2$ is $CF_3$, and wherein the method further comprises reacting $C_6F_5NH_2$, $CF_3$—CF=N—$C_2F_5$ and triethylamine in a molar ratio at or about 2:1:3.

6. The method of claim 1, wherein the method produces a high yield colorless crystalline solid.

7. A method of inhibiting growth of Gram-positive and Gram-negative bacteria, the method comprising:
providing a composition comprising as an antibacterial agent wherein $R^1$ is an alkyl or aryl group and $R^2$ is a fluoro alkyl group.

8. The method of claim 7, wherein the Gram positive bacteria is *Staphylococcus aureus* or *Bacillus subtilis*.

9. The method of claim 7, wherein the Gram negative bacteria is *Pseudomonas aeruginosa* or *Escherichia coli*.

10. A method of inhibiting the growth of Gram-positive and Gram-negative bacteria comprising administering an effective amount of a compound prepared by the method in claim 1, wherein the Gram-positive and Gram negative bacteria are selected from the group consisting of *Staphylococcus aureus, Pseudomonas aeruginosa, Bacillus subtilis* and *Escherichia coli*.

11. A method of synthesizing a poly-halogenated 1,3,5-triazapentadiene ligand comprising reacting $C_6F_5NH_2$, $CF_3$—CF=N—$C_2F_5$ and a tertiary amine in a molar ratio at or about 2:1:3.

12. A method of synthesizing a poly-halogenated 1,3,5-triazapentadiene ligand comprising reacting $C_6F_5NH_2$, $CF_3$—CF=N—$C_2F_5$ and triethylamine in a molar ratio at or about 2:1:3.

13. A method of synthesizing a poly-halogenated 1,3,5-triazapentadiene ligand metal complex comprising
reacting $C_6F_5NH_2$, $CF_3$—CF=N—$C_2F_5$ and a tertiary amine in a molar ratio at or about 2:1:3 to form a 1,3,5-triazapentadiene ligand; and
treating the formed 1,3,5-triazapentadiene ligand with a metal salt in the presence of a solvent to form a poly-halogenated 1,3,5-triazapentadiene ligand metal complex.

14. A method of synthesizing a poly-halogenated 1,3,5-triazapentadiene ligand metal complex comprising
reacting $C_6F_5NH_2$, $CF_3$—CF=N—$C_2F_5$ and triethylamine in a molar ratio at or about 2:1:3 to form a 1,3,5-triazapentadiene ligand; and
treating the formed 1,3,5 triazapentadiene ligand with a metal salt in the presence of a solvent to form a poly-halogenated 1,3,5-triazapentadiene ligand metal complex.

15. The method of claim 14, wherein the solvent is acetonitrile or tetrahydrofuran.

16. A method of making a polyhalogenated 1,3,5-triazapentadiene ligand metal complex comprising treating a poly-halogenated 1,3,5-triazapentadiene ligand, selected from the group consisting of $[N\{(CF_3)C(C_6F_5)N\}_2]H$ and $[N\{(C_3F_7)C(2,6-Cl_2C_6H_3)N\}_2]H$, with a metal ion in the presence of a solvent to form a poly-halogenated 1,3,5-triazapentadiene ligand metal complex.

17. The method of claim 16, wherein the wherein the solvent is acetonitrile or tetrahydrofuran.

18. The method of claim 14, wherein the poly-halogenated 1,3,5-triazapentadiene ligand metal complex is further complexed with a molecule selected from the group consisting of carbon monoxide, ethylene, acetonitrile, and phosphine.

19. The method of claim 16, wherein the poly-halogenated 1,3,5-triazapentadiene ligand metal complex is further complexed with a molecule selected from the group consisting of carbon monoxide, ethylene, acetonitrile, and phosphine.

20. A poly-halogenated 1,3,5-triazapentadiene ligand metal complex selected from the group consisting of $[N\{(C_3F_7)C(2-F,6-(CF_3)C_6H_3)N\}_2]CuCo$, $[N\{C_3F_7)C(C_6F_5)N\}_2]Cu(C_2H_4)$, $[N\{(C_3F_7)C(2-F,6-(CF_3)C_6H_3)N\}_2]Cu(CO)(NCCH3)$, $[N\{(C_3F_7)C(2-F,6-(CF_3)C_6H_3)N\}_2]CuNCCH_3$, $[N\{(C_3F_7)C(C_6F_5)N\}_2]Ag$, $[N\{(C_3F_7)C(2-F,6-CF_3C_6H_3)N\}_2]Ag$, and $[N\{(C_3F_7)C(2,6-Cl_2C_6H_3)N\}_2]Ag$.

21. A method of inhibiting the growth of Gram-positive and Gram-negative bacteria comprising administering an effective amount of a poly-halogenated 1,3,5-triazapentadiene ligand prepared by the method in claim 12, wherein the Gram-positive positive and Gram negative bacteria is selected from the group consisting of *Staphylococcus aureus, Pseudomonas aeruginosa, Bacillus subtilis* and *Escherichia coli*.

22. A method of inhibiting the growth of Gram-positive and Gram-negative bacteria comprising administering an effective amount of a poly-halogenated 1,3,5-triazapentadiene ligand complex prepared by the method in claim 14, wherein the Gram-positive and Gram negative bacteria is selected from the group consisting of *Staphylococcus aureus, Pseudomonas aeruginosa, Bacillus subtilis* and *Escherichia coli*.

23. A method of inhibiting the growth of Gram-positive and Gram-negative bacteria comprising administering an effective amount of a poly-halogenated 1,3,5-triazapentadiene ligand complex prepared by the method in claim 16, wherein the Grain-positive and Gram negative bacteria is selected from the group consisting of *Staphylococcus aureus, Pseudomonas aeruginosa, Bacillus subtilis* and *Escherichia coli*.

24. A method of inhibiting the growth of Gram-positive and Gram-negative bacteria comprising administering an effective amount of a poly-halogenated 1,3,5-triazapentadiene ligand complex of claim 20, wherein the Gram-positive and Gram-negative bacteria is selected from the group consisting of *Staphylococcus aureus, Pseudomonas aeruginosa, Bacillus subtilis* and *Escherichia coli*.

* * * * *